(12) United States Patent
Choi et al.

(10) Patent No.: US 7,491,164 B2
(45) Date of Patent: Feb. 17, 2009

(54) INFLATABLE PROSTHESIS FOR AIDING PENILE ERECTION AND AUGMENTATION

(75) Inventors: Hyung Ki Choi, Seoul (KR); Hyun Min Choi, Seoul (KR); Sung Ha Kim, Busan (KR)

(73) Assignee: SS Clinic Corp., Seoul (KR)

( * ) Notice: Subject to any disclaimer, the term of this patent is extended or adjusted under 35 U.S.C. 154(b) by 0 days.

(21) Appl. No.: 11/908,040

(22) PCT Filed: Mar. 8, 2006

(86) PCT No.: PCT/KR2006/000803

§ 371 (c)(1),
(2), (4) Date: Sep. 7, 2007

(87) PCT Pub. No.: WO2006/096001

PCT Pub. Date: Sep. 14, 2006

(65) Prior Publication Data

US 2008/0139880 A1    Jun. 12, 2008

(30) Foreign Application Priority Data

Mar. 8, 2005  (KR) ............... 20-2005-0006131 U
Jul. 14, 2005  (KR) ................. 10-2005-0063645

(51) Int. Cl.
*A61F 2/26* (2006.01)
(52) U.S. Cl. ........................................................ 600/40
(58) Field of Classification Search .............. 600/38–41; 623/23.64–23.68
See application file for complete search history.

(56) References Cited

U.S. PATENT DOCUMENTS

| 5,263,981 A | 11/1993 | Polyak et al. |
| 5,433,694 A | 7/1995 | Lim |
| 2003/0212463 A1 | 11/2003 | Seo |

*Primary Examiner*—John P Lacyk
(74) *Attorney, Agent, or Firm*—Weiner & Burt, PC; Irving M. Weiner; Pamela S. Burt (57) ABSTRACT

Provided is an inflatable prosthesis for aiding penile erection and augmentation for being disposed between the outer skin and the pair of corpus cavernosa of a patient's penis. The inflatable prosthesis comprises a contractible cylinder body (10) provided with a cavity (11) therein and a liquid passage (12) at the rear portion thereof; a preferably elastic or flexible head ring (20) with an annular body; a means for coupling the head ring with the front portion of the cylinder body (10); and a liquid pump (50) coupled with the liquid passage (12) of the cylinder body (10). According to the present invention, the possibility of causing damage to the penis, particularly the corpus cavernosum, may be reduced.

20 Claims, 6 Drawing Sheets

INFLATABLE PROSTHESIS FOR AIDING PENILE ERECTION AND AUGMENTATION

TECHNICAL FIELD

The present invention relates to an inflatable prosthesis for aiding erection and augmentation of a patient's penis (sexual organ), and more particularly, to an inflatable prosthesis for aiding erection and augmentation of the penis that may not cause damage to the corpus cavernosum, while increasing erectile stiffness of the sexual organ of a patient suffering from erectile dysfunction as well as augmenting the size thereof.

BACKGROUND ART

Recently, oral medicines for curing men's acute erectile dysfunction have been developed. Such medicines, however, are known to cause side effects and to be unsuitable for patients with heart diseases or blood circulatory problems. When such oral medicines are not efficacious, the patient may choose injections to be directly administered in the blood vessels of the corpus cavernosum of the penis to obtain artificial or forced erection.

When the oral medicines or injections fail to produce the desired results, penile implants are recommended as a last resort.

Such implants may be divided into two types: malleable one that can be straightened out and then reversed and inflatable one that can be stiffened and then made limp or flaccid.

DISCLOSURE OF INVENTION

Technical Problem

Conventional implants usually inserted into the corpus cavernosum, as the erectile tissue, have the possibility of damaging the corpus cavernosum in the course of implanting operation and/or working, and thus, leading the sexual organ to permanent erectile dysfunction, especially when they have to be removed due to side effects like infection or contagion or mechanical failures after surgery.

In addition, inserting operation of an implant into the corpus cavernosum requires general anesthetizing of the patient, and complicated and long surgical procedures with the prolonged term of recuperation. These are factors prohibiting many patients from undergoing such kind of surgical operation as above.

An object of the present invention is to provide an inflatable prosthesis for aiding penile erection and augmentation which may require a simple surgical operation.

Another object of the present invention is to provide an inflatable prosthesis for aiding penile erection and augmentation with which danger of the side effects and complications may be reduced.

Another object of the present invention is to provide an inflatable prosthesis for aiding penile erection and augmentation which may not cause damage to the own erectility of the corpus cavernosum.

Still another object of the present invention is to provide an inflatable prosthesis for aiding penile erection and augmentation with which the sexual organ may be easily made to erect or contract.

Technical Solution

The above and other objects are achieved by the inflatable prosthesis for aiding penile erection and augmentation of the present invention, which may be disposed between the outer skin and the pair of the corpus cavernosa (more precisely tunica albuguinia of corpus cavernosa) of a penis to make the organ to erect or contract alternately and simultaneously or optionally augment the size of the erect penis.

According to an aspect of the present invention, there is provided an inflatable prosthesis for aiding penile erection and augmentation, comprising; a contractile cylinder body provided with a hollow or cavity for containing a liquid therein, a liquid passage at the rear portion of the cavity and a tapered slim front portion; a head ring with an annular body coupled to the end of the front portion of the cylinder body; a means for coupling the head ring with the end of the cylinder body; and a liquid pump coupled with the liquid passage of the cylinder body, wherein the cylinder body is arranged to be inserted and disposed between the outer skin and the pair of the corpus cavernosa of the patient's penis.

The cylinder body may have various sectional shapes which may be determined to be circular, square, pentagonal or hexagonal one as necessary and/or desired, and the cavity in the cylinder body may as well have such shapes, different from or similar to that of the cylinder body.

The front or head portion of the cylinder body may be formed with a shape suitable to be coupled to the head ring, for example, gradually tapering from the body portion to the front portion, where the end of the front portion thereof has an annular protrusion or recession to fit securely into a corresponding annular recession or protrusion in a coupling hole of the head ring. Further, the tapered head portion of the cylinder body may have a stepped shape with different angles between the adjacent slants, while the rear portion thereof may have a round shape.

The cylinder body is arranged to be provided with an elastic liquid passage at the rear portion thereof, through which a liquid may flow in or out, and which is desirably formed inclined rearward, extending outwardly from the cylinder body in order to facilitate connecting thereof with the pump via a conduit. The passage may have an inner surface with protrusions or recessions to fit into the corresponding recessions or protrusions of the conduit inserted therein. Alternatively, the passage may have an outer surface formed with protrusions or recessions to fit into the corresponding recessions or protrusions on the inner surface of the conduit. Further, the passage may extend to and be directly connected with the discharge hole of the pump.

The annular body of the head ring may have the shape of an open circle or an arc like the letter "C" for easier coupling with the head of the sexual organ in the course of the surgical operation as well as a closed circle. The head ring may have a round skirt, extending from the wall of the annular body of the head ring with the inner and outer circumferential surfaces formed perpendicularly to the radial plane of the head ring as a coupling portion with the head of the penis, provided for wider contact of the head ring with the penis. Either or both the opposite end portions of the open annular body of the head ring may preferably have a protrusion with a diameter larger than the remaining circular portion, making the size thereof bigger.

The head ring may be arranged to have an open or closed hole with or without a recession to receive the slim end of the front portion of the cylinder body, acting as a means for coupling the head ring with the cylinder body.

The head ring may be desirably provided with a hollow or cavity, open or closed, in the annular body for receiving a liquid from the pump through a hole which may be one described as the coupling means hereinbefore, or the other and communicates with the hollow in the cylinder body through a front opening of the cylinder body, or only for holding the liquid therein. With the open cavity in the annular body, the head ring can be filled with a pressurized fluid from the pump, helping the head ring swell and expand with the better effects of augmenting the penis as a whole. The cavity in the annular body may of course hold a liquid therein without allowing to flow out.

The liquid used for the inflatable prosthesis may be physiological saline solution, water, jelly or other biocompatible fluids, preferably saline solution, while the pump may be provided with a discharge port having a check valve or the like for preventing undesired backward flowing of the liquid discharged there from under pressure and allowing the liquid to return from the cylinder body by means of an outside operation of the pump, and a means for pressurizing the liquid stored therein, while the pump may be replaced with a contratile container of the liquid so that the volume of the liquid may be reduced by a pressure given from the outside for pressurizing the liquid contained therein.

An example of the pump is disclosed in the Korean utility model registration no. 20-332863 published on Oct. 31, 2003, the contents which constitute a reference to the present invention.

The size of the prosthesis according to the present invention may be determined according to the patient's desire or anatomical conditions, but may usually have a cylinder body with a diameter from 5 to 6 mm and a length between 60 to 70 mm in a "flaccid" state, which may respectively increase to between 7 and 8 mm and 80 to 90mm in an "erect" state.

The prosthesis has desirably a support which is arranged to be fastened to the pelvic girdle of the patient, to which the rear end of the cylinder is held, in order to prevent shaking or rocking of the prosthesis due to repetitive forward and backward movements thereof during sexual intercourse or long use. The support may be a plate provided with a crater-shaped recess formed on one side for receiving the rear portion of the cylinder body and a fastening portion disposed on the opposite side for the pelvic girdle so that the cylinder body may be tilted for a predetermined degree. The rear end of the cylinder body is inserted into the recess and the fastening portion is attached to the pelvic girdle in order to prevent rearward dislocation of the cylinder body.

The cylinder body is preferably made of an elastic biocompatible material, such as silicon, polyurethane, and other similar materials.

A fabric reinforcing layer may be added in the silicon or polyurethane wall of the cylinder so as to prevent the cylinder body from undesirable inflating in the circumferential direction and help it expand in the longitudinal direction. It is desirable to form the fabric reinforcing layer with highly elastic urethane fibers such as spandex, for example, Lycra made by Dupont.

BRIEF DESCRIPTION OF THE DRAWINGS

Hereinafter, preferred examples of inflatable prosthesis for aiding penile erection and augmentation according to the present invention will be described in detail with reference to the accompanying drawings, in which.

BEST MODE FOR CARRYING OUT THE INVENTION

Figure 1:
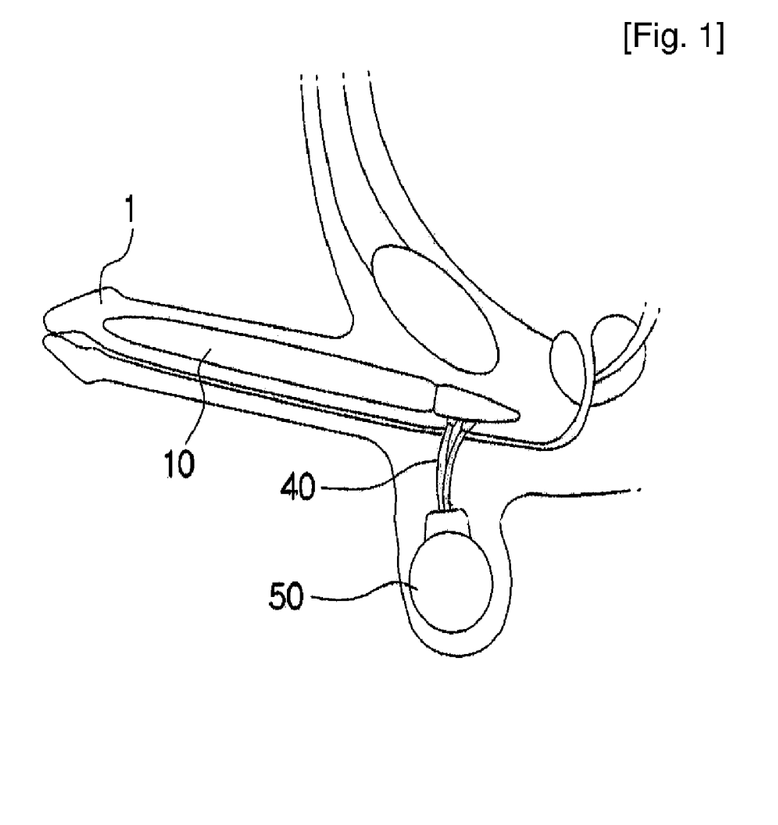
FIG. 1 is a sectional view showing an erection aid of the prior art in working.

FIG. 1 is a sectional view showing an erection aid of the prior art in working.

Referring to FIG. 1, it is seen that a cylinder body 10 of the erection aid prosthesis is inserted into and disposed in the corpus cavernosum (an erectile tissue) and connected to a pump 50 located in the scrotum through a conduit 40. A liquid that is pressurized by the pump 50 flows through the conduit 40 into the cylinder body 10 to expand it for erecting the penis. However, the aid has the disadvantage that the corpus cavernosum having the cylinder body therein can lose its innate erectile ability after prolonged use of the prosthesis, due to the possible damage thereto caused by the implanting operation, the movement of the cylinder body therein, friction of the cylinder with the cavernosum, and pressure from repeated expansion and contraction of the cylinder body.

Figure 2:
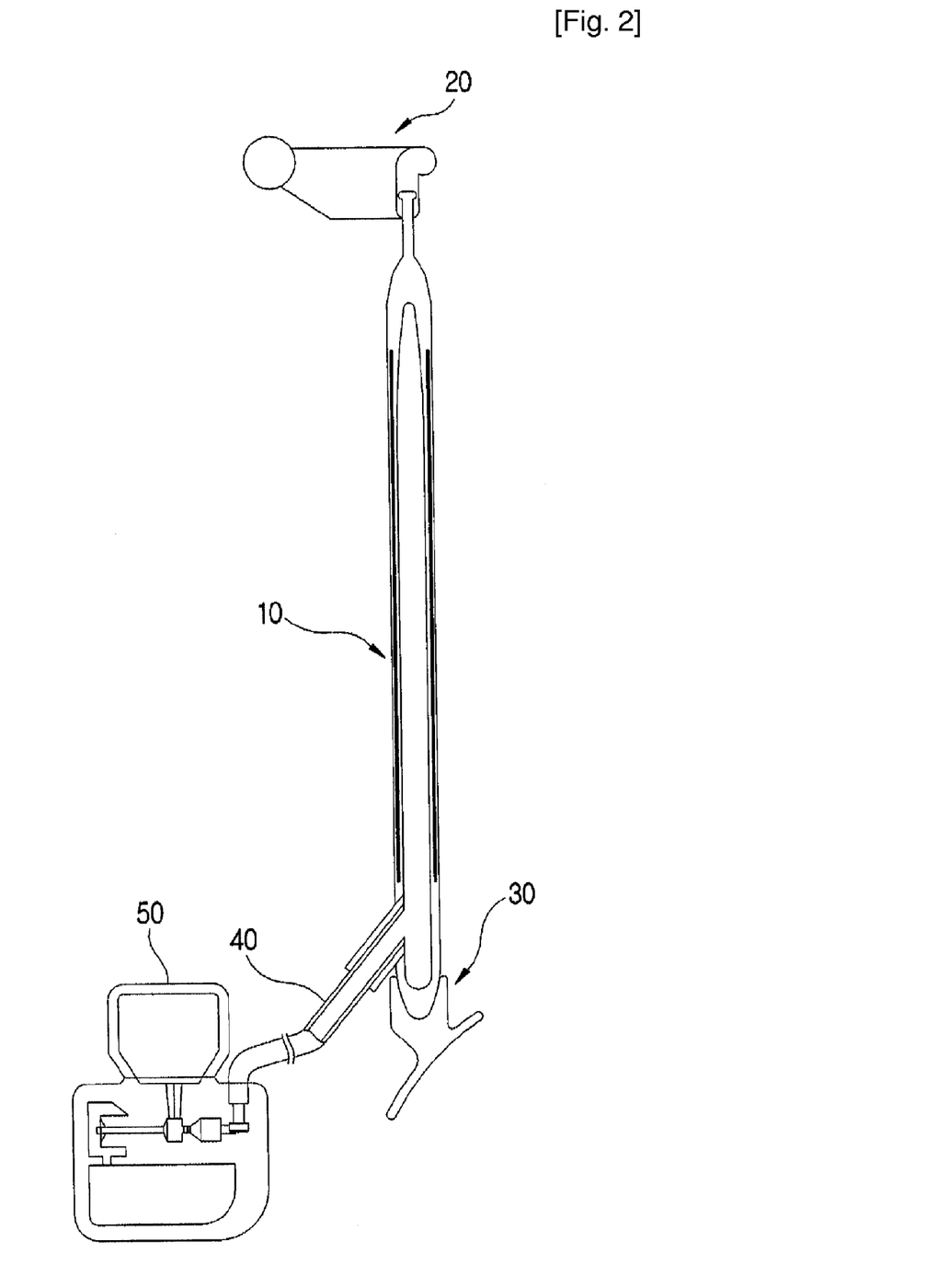
FIG. 2 is a sectional view showing an inflatable prosthesis for aiding penile erection and augmentation according to an embodiment of the present invention, when it is inflated for working.
Figure 3:
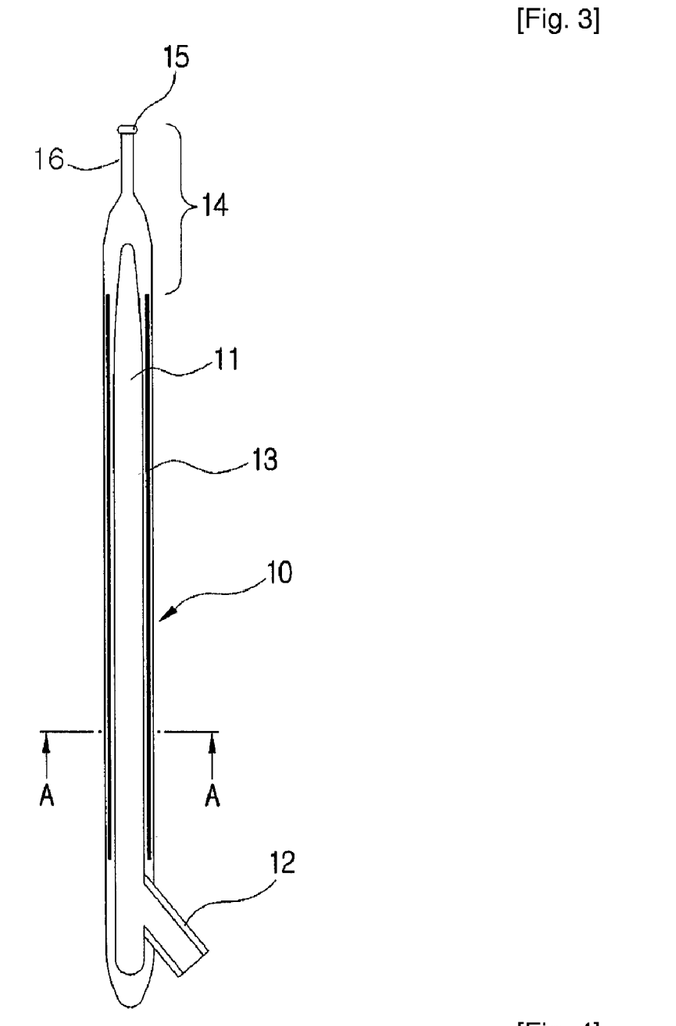
FIG. 3 is sectional view showing the contractile cylinder body of the inflatable prosthesis in FIG. 2.

FIG. 2 is a sectional view showing an inflatable prosthesis for aiding penile erection and augmentation according to an embodiment of the present invention, as inflated for working, and FIG. 3 is a sectional view showing the contractile cylinder body of the inflatable prosthesis in FIG. 2.

In the drawings, a head ring 20 is coupled to the front portion of a cylinder body 10, and the body 10 is connected at a liquid passage 12 of the cylinder body to a pump 50 through a conduit 40. A support 30 is provided at the rear portion of the cylinder body.

A hollow or cavity 11 is formed in the cylinder body with a rearward inclined passage 12 for allowing a liquid to flow back and forth to the pump. The passage 12 extends from the rear portion of the hollow 11.

An opening is to be provided preferably at the end of the front portion of the cylinder body for allowing the hollow or cavity 11 to communicate with a hollow or cavity 27 in the head ring 20 which is fitted to the front portion of the cylinder body, as will be described in detail hereinafter with reference to FIGS. 5 through 10. A fabric reinforcing layer 13 is desirably formed in the cylinder body, as can be seen from FIG. 4, the sectional view of the cylinder taken along line A-A in FIG. 3.

The cylinder body 10 has a taper front portion 14, which is shown to have two bent points in FIG. 3, with a slim circular end 16 provided with a protrusion or knob 15 at its tip. The protrusion or knob 15 is arranged to fit into and couple to a hole formed in the head ring as a coupling means and firmly combine the head ring with the cylinder body 10, as will be described hereinafter.

Figure 4:
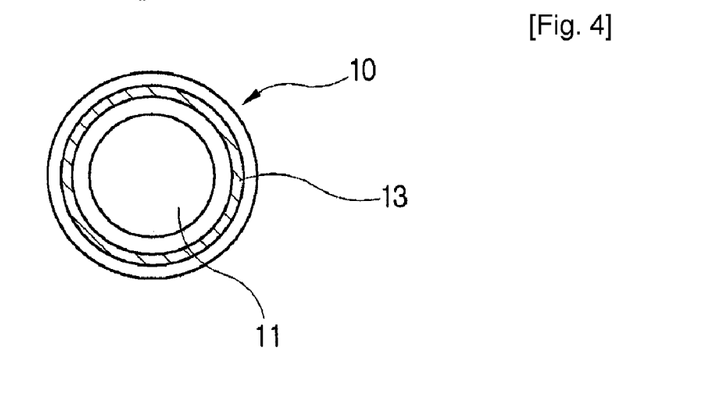
FIG. 4 is a sectional view of the cylinder body in FIG. 3 taken along line A-A.

Referring to the cylinder body 10 shown in section in FIG. 4, the wall of the cylinder body comprises two layers formed of biocompatible material such as silicon for surrounding and confining the hollow or cavity 11 and a reinforcing layer 13 made of fiber such as spandex, disposed between the two silicon layers to form a three-layered structure of the cylinder body.

Figure 5:
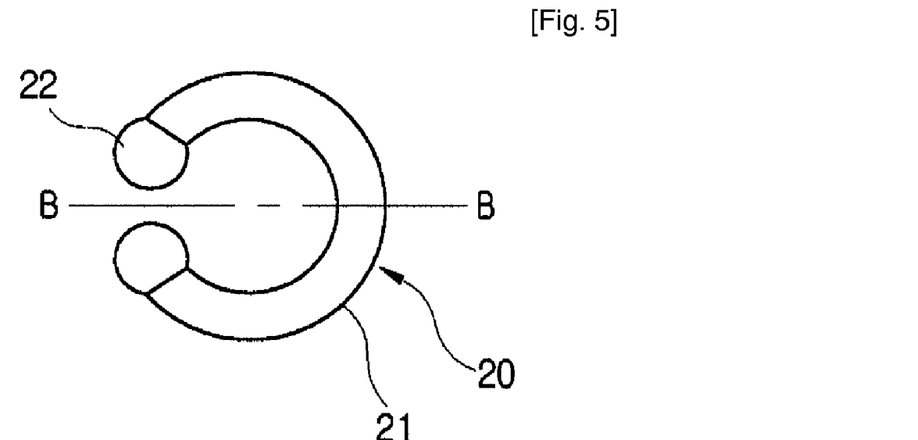
FIG. 5 is a plan view of a head ring of the inflatable prosthesis in FIG. 2.
Figure 6:
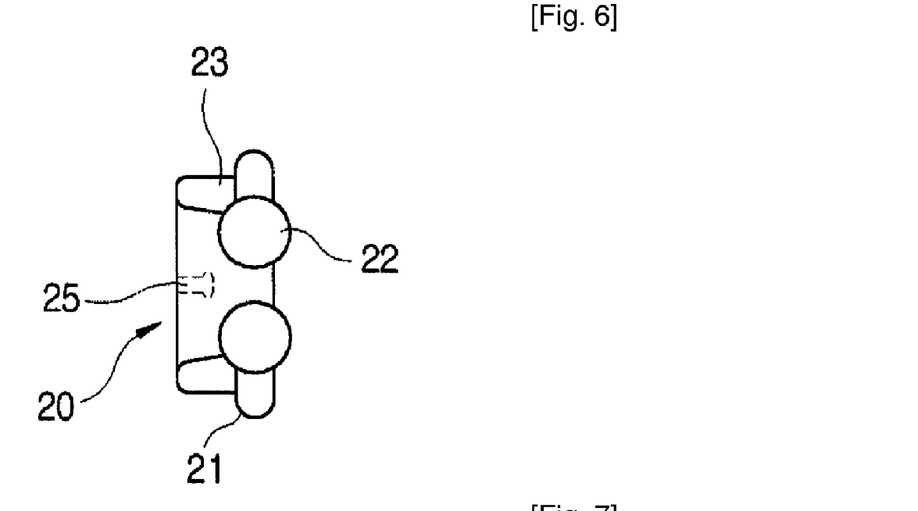
FIG. 6 is a left side view of the head ring in FIG. 5.
Figure 7:
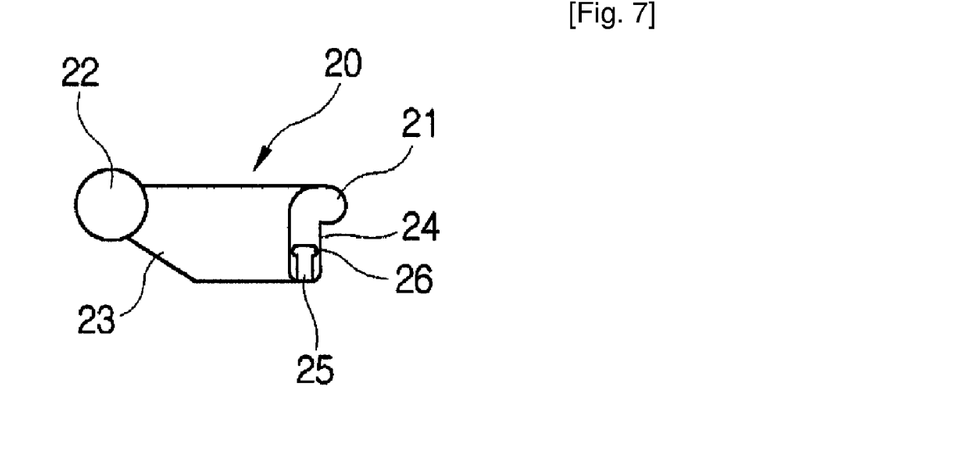
FIG. 7 is a sectional view of the head ring in FIG. 5 taken along line B-B.

FIGS. 5 through 7 are respectively a plan view, a left side view, and a front sectional view of an example of the head ring 20 according to the present invention.

Referring to FIG. 5, the head ring 20 has preferably a "C" shape in section. The head ring can have a bigger diameter when the gap between the opposite end portions thereof is widened so that it may be easily positioned and arranged near the glans of the penis in the implanting process of the surgical operation. The annular hollow body 21 of the head ring 20 has an even thickness over the circular portion, with its end portions 22 formed bigger than the annular portion, which makes the penis enlarged more.

Referring to FIG. 6, an optional round skirt 23 is provided perpendicularly to the annular body of the head ring 20 with a thickness, similar to the diameter of the annular body 21 and the increased surface area thereof contacting the penis for securely supporting the cylinder body 10 shown in FIG. 3 to the penis.

Referring to FIG. 7, a coupling portion 24 is provided in the central portion of the skirt perpendicular to the radial direction of the annular body of the head ring 20. The coupling portion 24 includes a closed hole 25 with a recession 26.

The end 16 of the front portion 14 of the cylinder body is inserted together with the protrusion 15 into the hole 25 of the coupling portion 24 so that the protrusion 15 of the cylinder body 10 may be disposed in the recession 26 in the skirt of the head ring 20 and the cylinder body 10 and the head ring 20 may be securely coupled with each other. Before or after the above coupling is completed, a silicon adhesive may be applied to the connecting portion to strengthen the coupling.

Figure 8:
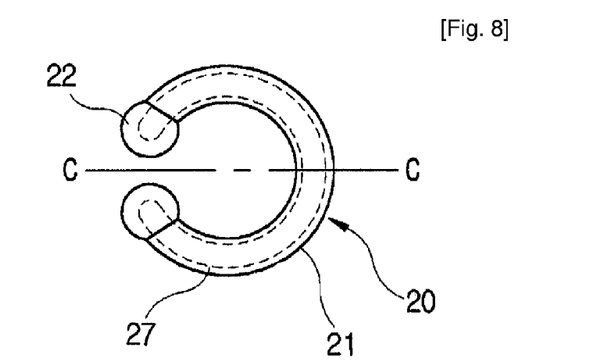
FIG. 8 is a plan view of a variation of the head ring in FIG. 5.
Figure 9:
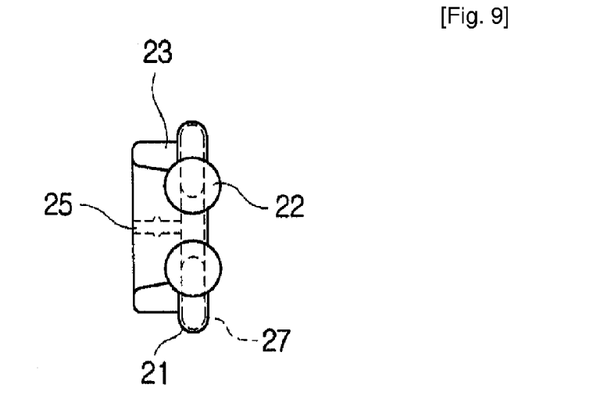
FIG. 9 is a left side view of the head ring in FIG. 8.
Figure 10:
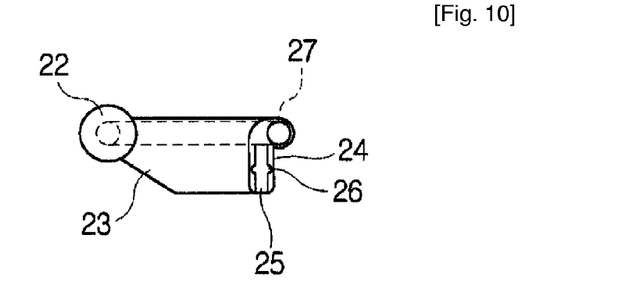
FIG. 10 is a sectional view of the head ring in FIG. 8 taken along line C-C.

FIGS. 8 through 10 are views of another example of the head ring 20 with an annular body 21 having a hollow or cavity 27 according to the present invention.

Referring to FIGS. 8, 9 and 10, the head ring 20 is provided with a cylinder coupling portion 24 having a hole 25 communicating with the cavity 27 in the annular body 21 and an annular recession 26 formed in the middle thereof.

The end 16 and its the protruded tip 15 are received and fixed in the rear part of the coupling hole 25 and the recession 26 respectively in the similar way as the head ring in FIGS. 5, 6 and 7.

Figure 11:
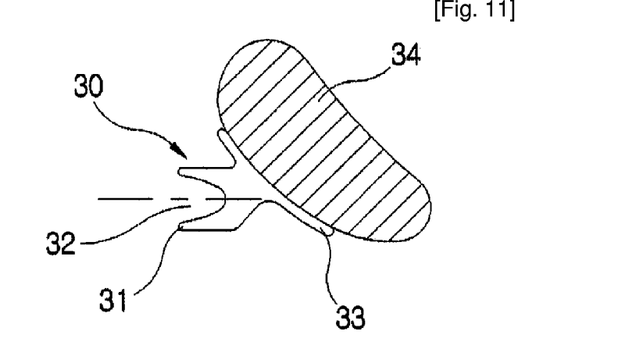
FIG. 11 is a sectional view showing a support of the inflatable prosthesis in FIG. 2 attached to a pelvic girdle.
Figure 12:
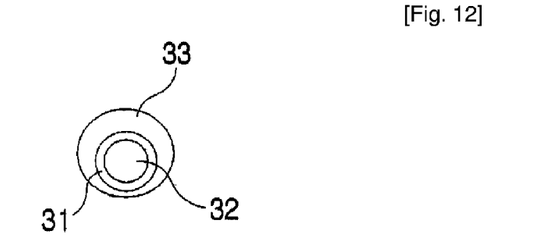
FIG. 12 is a plan view of the support in FIG. 11.

FIG. 11 is a sectional view showing a support 30 of the inflatable prosthesis for aiding penile erection and augmentation in FIG. 2 attached to a pelvic girdle, and FIG. 12 is a side view of the support in FIG. 11.

Referring to FIGS. 11 and 12, the annular support wall 31 confines and forms a recess 32 for the support 30 for receiving and supporting the rear portion of the cylinder body 10 (not shown) therein. A fastening plate 33 is sealed to the pelvic girdle 34 with an adhesive or other relevant means applicable to the present invention and prevents the cylinder body 10 from slipping rearward. The support 30 may also be made of silicon or other elastic and biocompatible materials.

Figure 13:
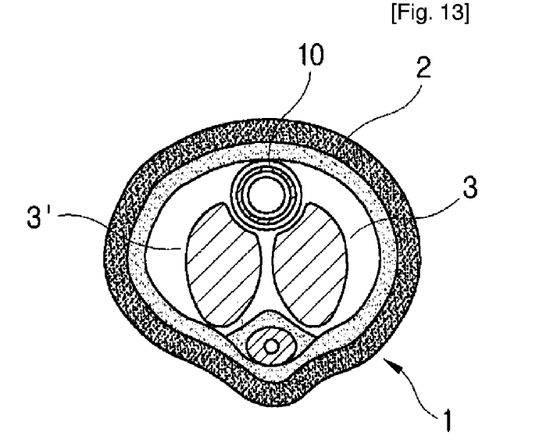
FIG. 13 is a sectional view of a penis with a inflatable prosthesis for aiding penile erection and augmentation according to the present invention implanted therein.

FIG. 13 is a sectional view of a penis with an implanted inflatable prosthesis for aiding penile erection and augmentation according to the present invention. That is, the cylinder body 10 is disposed between the skin 2 and the pair of corpus cavernosa 3 and 3'. In this way, the cylinder body 10 may not cause damage to the corpus cavernosa 3 and 3' and can be implanted with simple surgical processes.

Figure 14:
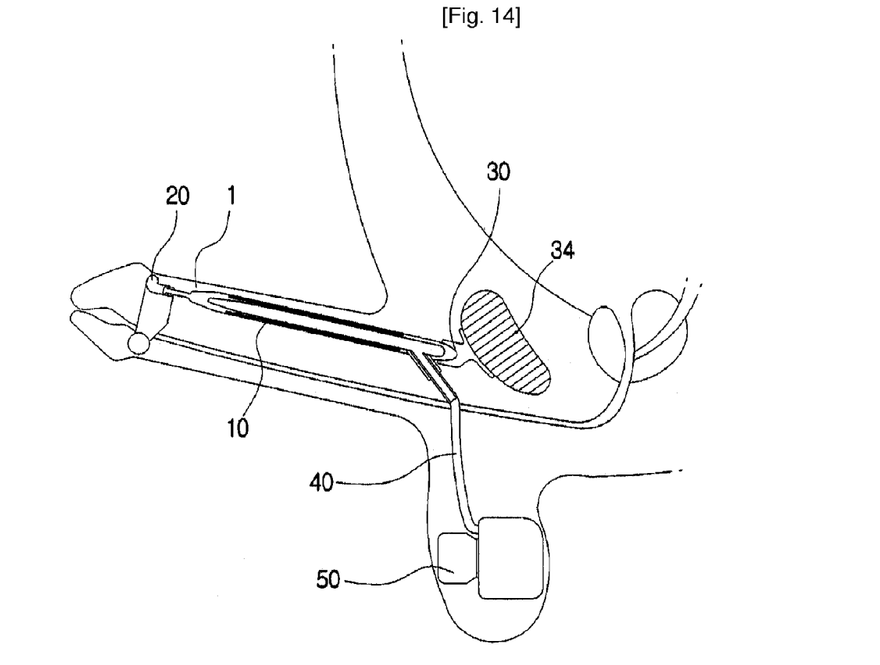
FIG. 14 is a sectional view showing the inflatable prosthesis in FIG. 2 in working.

FIG. 14 is a sectional view showing the inflatable prosthesis for aiding penile erection and augmentation in FIG. 2 in working. Referring to FIG. 14, the head ring 20 and the support 30 are respectively coupled with the front end and the rear portion of the cylinder body 10. When the pump 50 connected to the hollow or cavity in the cylinder body through the conduit and the passage is operated, the liquid therein is pressurized and flows into the cylinder body (optionally, the head ring) to fill the cylinder with the liquid and expand the same to induce simultaneous erection of the penis. As desired, a valve disposed in the pump or at an exit end of the pump is activated to release the erection by allowing the liquid in the cylinder to return to its storage space in the pump.

While the present invention has been described and illustrated herein with reference to the preferred embodiment thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents.

For example, the annular body of the head ring may be made in a polygonal shape, or have a bumpy or angular surface or be provided with a closed hollow or cavity charged with a liquid, while various kinds of small liquid pumps may be employed for this invention. Further, the coupling means may be provided in various ways and locations, i.e., forming a coupling hole in the annular body of the head ring without the skirt, or in the end of the front portion of the cylinder body for receiving and holding a corresponding fixing rod extending from the annular body or the skirt of the head ring.

INDUSTRIAL APPLICABILITY

An advantage of the inflatable prosthesis for aiding penile erection and augmentation according to the present invention is that the prosthesis may be inserted between the outer skin and the pair of the corpus cavernosa of the penis through a relatively easy and simple surgical operation so that the patient's postoperative recovery is good and speedy and the likelihood of postoperative complications may be reduced.

The inflatable prosthesis according to the present invention may not only help the penis erect but also can lengthen and widen the erect size thereof as desired.

Further, the penis prosthesis according to present invention, implanted as above-described, may be easily removed without causing damage to the corpus cavernosa and impeding the natural erectile ability of the subject's penis.

The invention claimed is:

1. An inflatable prosthesis for aiding penile erection and augmentation for being disposed between the outer skin and the pair of cavernosa of a patient's penis, comprising;
    a contractible cylinder body, which is provided with a hollow or cavity for a liquid, a slim front portion and a liquid passage communicating with the hollow or cavity;
    a preferably elastic head ring with an annular body;
    a means for coupling said head ring with the front portion of said cylinder body;
    and a liquid pump for supplying a liquid to said cylinder body through said passage and withdrawing the liquid in said cylinder body through said passage.

2. The inflatable penile prosthesis according to claim 1, characterized in that the annular body of said head ring forms a closed circle.

3. The inflatable penile prosthesis according to claim 1, characterized in that the annular body of said head ring forms an open circle or arc.

4. The inflatable penile prosthesis according to claim 3, characterized in that either or both of the two opposite ends of the annular body of said head ring is provided with a protrusion.

5. The inflatable penile prosthesis according to claim 1, characterized in that said cylinder body is made of an elastic biocompatible material.

6. The inflatable penile prosthesis according to claim 5, wherein said biocompatible material is silicon or polyurethane.

7. The inflatable penile prosthesis according to claim 6, wherein said the cylinder body further comprises a fabric reinforcing layer within the silicon or polyurethane material layer.

8. The inflatable penile prosthesis according to claim 1, characterized in that said head ring is provided with a round skirt extending from the wall of the annular body of said head ring.

9. The inflatable penile prosthesis according to claim 1, characterized in that said head ring is provided with a hollow or cavity in the annular body.

10. The inflatable penile prosthesis according to claim 9, characterized in that the front portion of said cylinder body is provided with a hollow or cavity and a tip opening which communicate with the hollow or cavity of said cylinder body and that of said head ring.

11. The inflatable penile prosthesis according to claim 1, characterized in that said coupling means comprises a hole in said head ring which receives and fixedly holds the end of the front portion of said cylinder body with or without an adhesive applied.

12. The inflatable penile prosthesis according to claim 11, characterized in that said coupling hole is either closed at one end or open.

13. The inflatable penile prosthesis according to claim 11, characterized in that said coupling hole is provided in said skirt.

14. The inflatable penile prosthesis according to claim 11, characterized in that said coupling hole in said head ring is provided with a recession for receiving an adhesive and/or the corresponding protrusion formed at the end of the front portion of said cylinder body.

15. The inflatable penile prosthesis according to claim 14, characterized in that said recession and protrusion are of an annular shape respectively so that they may fit into each other.

16. The inflatable penile prosthesis according to claim 2, characterized in that said coupling means comprises a hole in said head ring which receives and fixedly holds the end of the front portion of said cylinder body with or without an adhesive applied.

17. The inflatable penile prosthesis according to claim 3, characterized in that said coupling means comprises a hole in said head ring which receives and fixedly holds the end of the front portion of said cylinder body with or without an adhesive applied.

18. The inflatable penile prosthesis according to claim 4, characterized in that said coupling means comprises a hole in said head ring which receives and fixedly holds the end of the front portion of said cylinder body with or without an adhesive applied.

19. The inflatable penile prosthesis according to claim 5, characterized in that said coupling means comprises a hole in said head ring which receives and fixedly holds the end of the front portion of said cylinder body with or without an adhesive applied.

20. The inflatable penile prosthesis according to claim 6, characterized in that said coupling means comprises a hole in said head ring which receives and fixedly holds the end of the front portion of said cylinder body with or without an adhesive applied.

\* \* \* \* \*